United States Patent [19]
Yoon

[11] Patent Number: 5,849,019
[45] Date of Patent: Dec. 15, 1998

[54] MULTIFUNCTIONAL SPRING CLIPS AND CARTRIDGES AND APPLICATIONS THEREFOR

[76] Inventor: InBae Yoon, 2101 Highland Ridge Dr., Phoenix, Md. 21131

[21] Appl. No.: 944,673

[22] Filed: Oct. 7, 1997

Related U.S. Application Data

[63] Continuation of Ser. No. 807,083, Feb. 27, 1997, Pat. No. 5,725,542, which is a continuation of Ser. No. 401,002, Mar. 9, 1995, Pat. No. 5,695,505.

[51] Int. Cl.$^6$ .................................................. A61B 17/12
[52] U.S. Cl. ........................................... 606/157; 606/151
[58] Field of Search ..................................... 606/151, 157, 606/120, 139; 128/843; 227/901, 902; 29/243.5, 243.56; 267/53; 140/82; 24/455, 501, 511, 533, 545, 546, 547

[56] References Cited

U.S. PATENT DOCUMENTS

| | | |
|---|---|---|
| 119,938 | 10/1871 | Mellish . |
| 607,297 | 7/1898 | Taylor . |
| 664,885 | 1/1901 | McGrath . |
| 1,152,492 | 9/1915 | Deming . |
| 3,032,039 | 5/1962 | Beaty ...................................... 606/221 |
| 3,091,828 | 6/1963 | Soltis . |
| 3,446,212 | 5/1969 | Le Roy . |
| 3,604,425 | 9/1971 | LeRoy . |
| 3,958,576 | 5/1976 | Komiya . |
| 4,064,881 | 12/1977 | Meredith . |
| 4,217,902 | 8/1980 | March . |
| 4,396,139 | 8/1983 | Hall et al. . |
| 4,484,581 | 11/1984 | Martin et al. . |
| 4,612,932 | 9/1986 | Caspar et al. . |
| 4,637,395 | 1/1987 | Caspar et al. . |
| 4,777,949 | 10/1988 | Perlin ...................................... 606/158 |
| 4,777,950 | 10/1988 | Kees, Jr. . |
| 4,791,707 | 12/1988 | Tucker . |
| 4,869,268 | 9/1989 | Yoon . |
| 4,961,743 | 10/1990 | Kees, Jr. et al. . |
| 4,990,152 | 2/1991 | Yoon . |
| 5,026,379 | 6/1991 | Yoon . |
| 5,062,846 | 11/1991 | Oh et al. ................................. 606/158 |
| 5,100,418 | 3/1992 | Yoon et al. . |
| 5,171,250 | 12/1992 | Yoon . |
| 5,217,030 | 6/1993 | Yoon . |
| 5,217,473 | 6/1993 | Yoon . |
| 5,334,209 | 8/1994 | Yoon . |
| 5,342,373 | 8/1994 | Stefanchik et al. . |
| 5,366,458 | 11/1994 | Korthoff et al. . |
| 5,366,459 | 11/1994 | Yoon . |
| 5,464,416 | 11/1995 | Steckel .................................... 606/158 |
| 5,465,516 | 11/1995 | Steckel . |
| 5,487,746 | 1/1996 | Yu et al. ................................. 606/151 |

FOREIGN PATENT DOCUMENTS

| | | |
|---|---|---|
| 2573647 | 11/1984 | France . |
| 2144172 | 2/1985 | United Kingdom . |

*Primary Examiner*—Michael Buiz
*Assistant Examiner*—Daphna Shai

[57] ABSTRACT

A multifunctional spring clip for use in endoscopic and open operative procedures includes a body having opposed portions and a base connecting the opposed portions. Each opposed portion includes an outer segment and an inner segment connected to the outer segment and carrying a grasping surface. The clip is normally disposed in a grasping position wherein the grasping surfaces are biased toward one another, is movable from the grasping position to a receiving position wherein the grasping surfaces are moved away from one another to receive a structure therebetween and is movable from the receiving position toward the grasping position due to the bias to grasp the structure between the grasping surfaces. An applicator for the multifunctional spring clip includes a distal end carrying forceps for engaging the opposed portions of the clip. The forceps engage the clip in the grasping position and are movable from a closed position to an open position to move the clip from the grasping position to the receiving position to receive the structure between the grasping surfaces. The forceps are movable from the open position to the closed position to permit the clip to move from the receiving position toward the grasping position to grip the structure between the grasping surfaces. A cartridge storing a plurality of multifunctional spring clips is insertable in the applicator for selectively releasing one of the clips from the cartridge into engagement with the forceps.

20 Claims, 13 Drawing Sheets

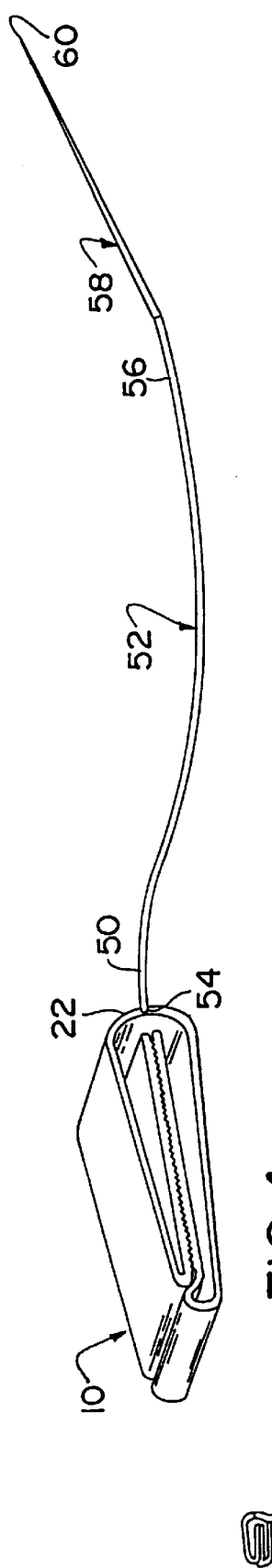
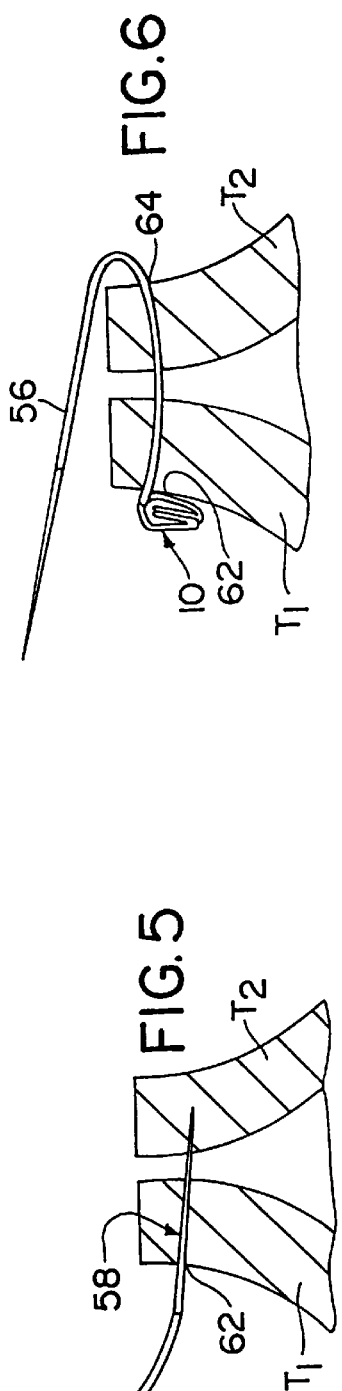
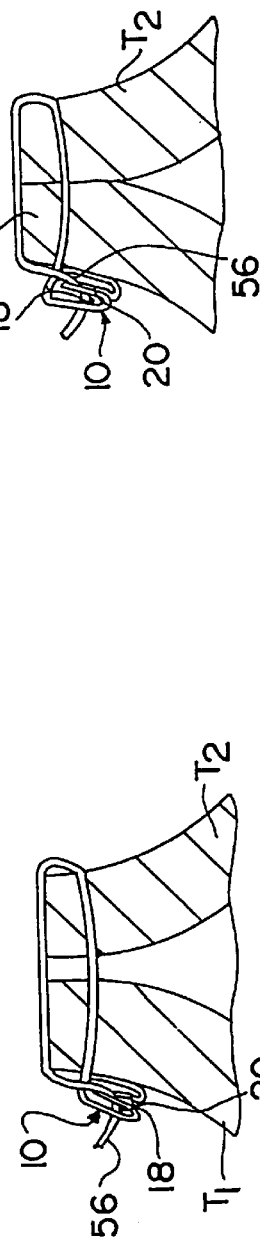
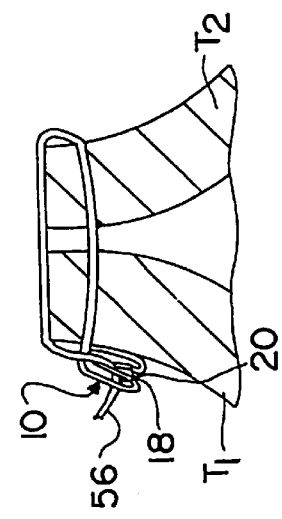

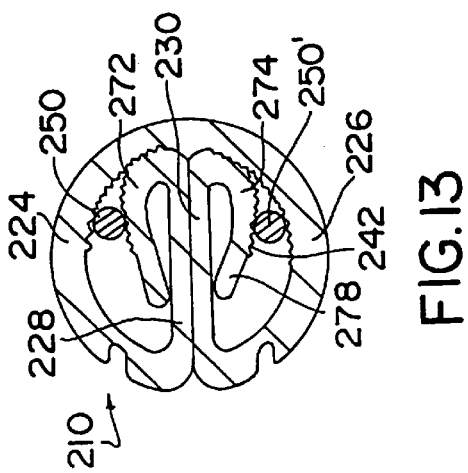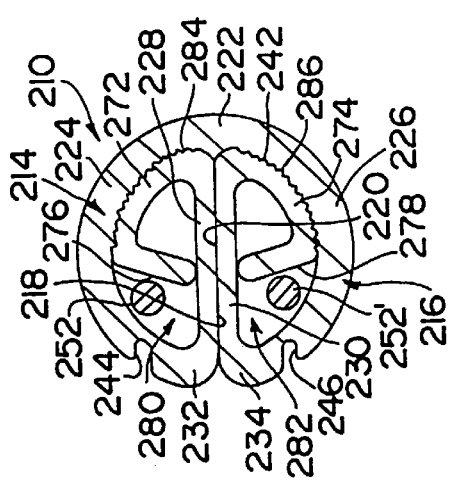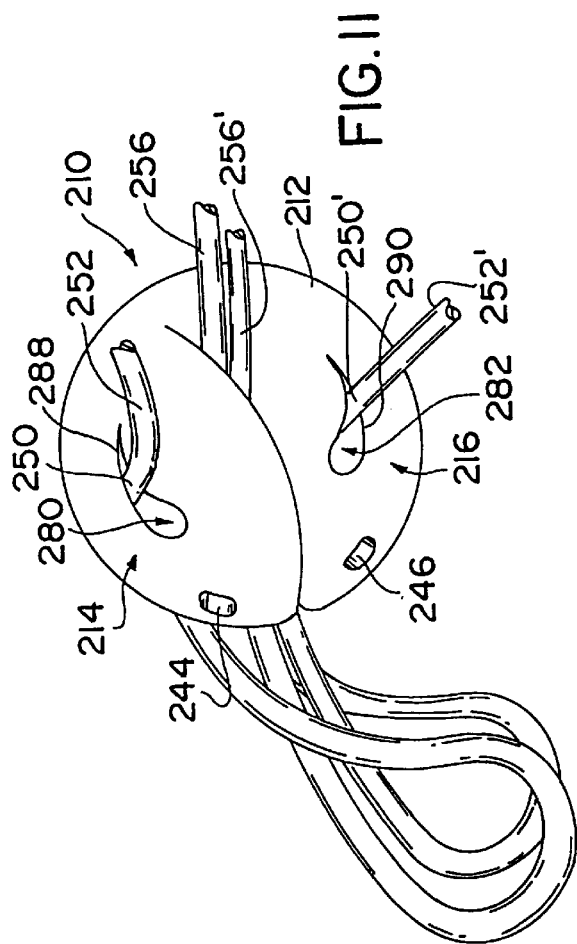

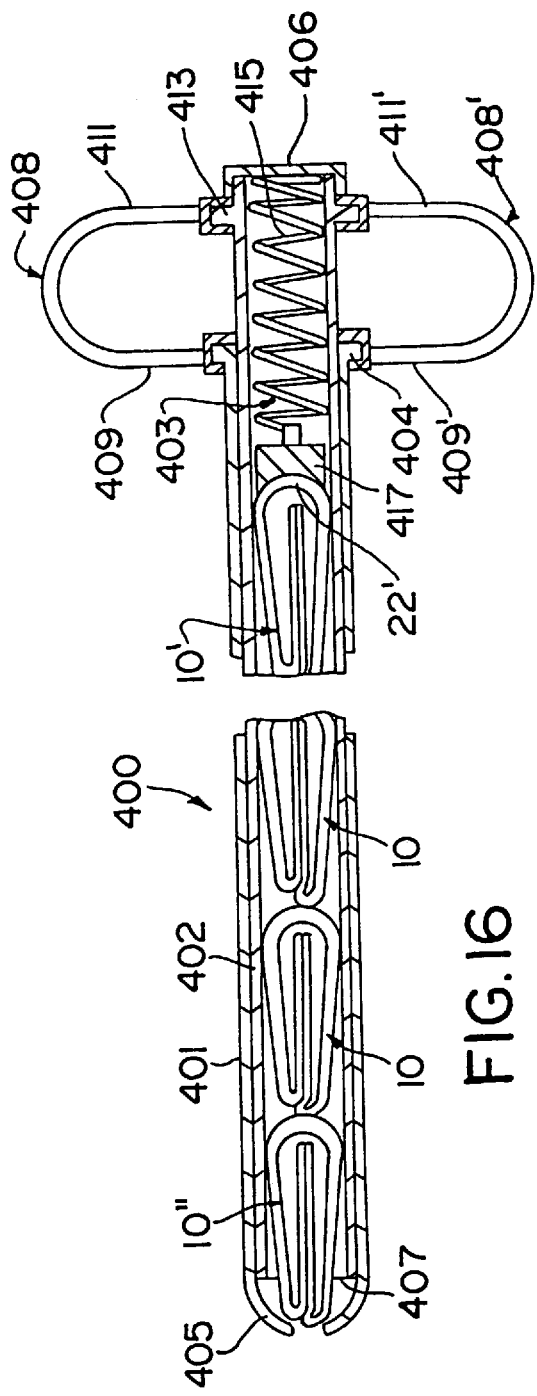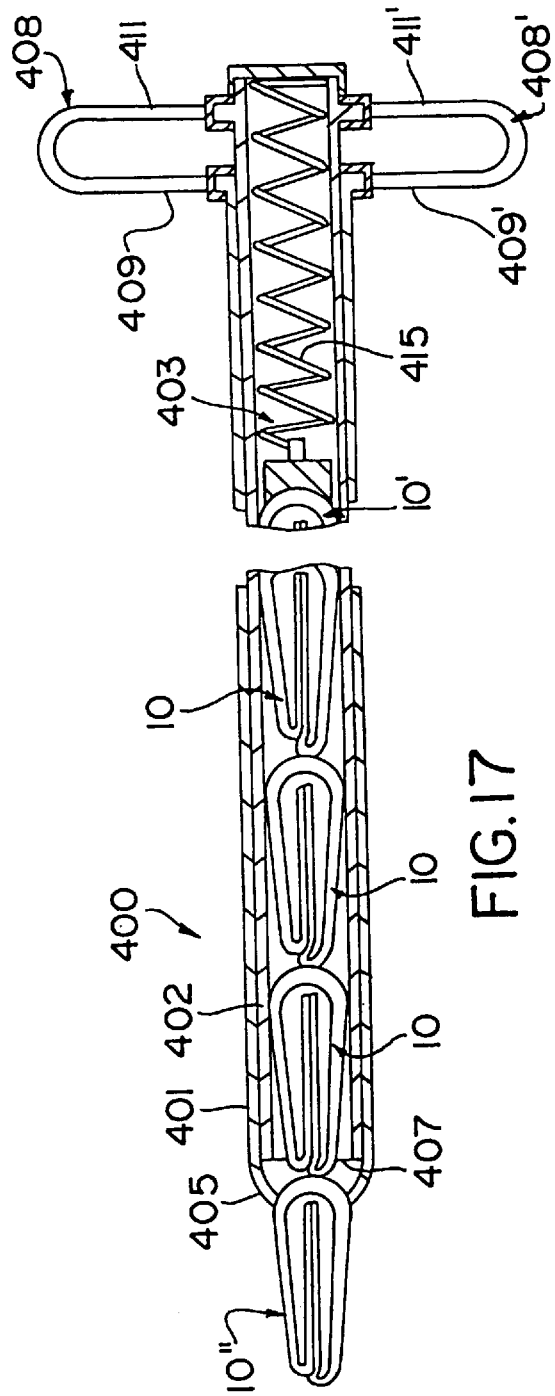

MULTIFUNCTIONAL SPRING CLIPS AND CARTRIDGES AND APPLICATIONS THEREFOR

This application is a continuation of prior application Ser. No. 08/807,083, filed Feb. 27, 1997, now U.S. Pat. No. 5,725,542, which is a continuation of prior application Ser. No. 08/401,002, filed Mar. 9, 1995, now U.S. Pat. No. 5,695,505, the disclosures of which are incorporated herein by reference.

BACKGROUND OF THE INVENTION

1. Field of the Invention

The present invention relates generally to clips for use in endoscopic and open surgical procedures and, more particularly, to clips biased to a closed position and movable to an open position to receive a structure with the clips being movable due to the bias from the open position toward the closed position to grasp the structure and to cartridges and applicators therefor.

2. Description of the Prior Art

During the course of many endoscopic and open surgical procedures, it is frequently necessary to apply clips to anatomical structure to occlude, ligate, clamp, close or approximate the anatomical structure, for example. Where utilized to close vessels, it is extremely important that the clips ensure complete closure of the vessels so as to prevent leakage of fluid therethrough. Additionally, it is essential for patient safety that the clips remain closed until intentionally opened or removed; and, therefore, the clips must not inadvertently pop open or break. It is also important that the clips remain in position and not slip, slide or otherwise move relative to the structure being held.

Various spring clips have been proposed to enhance gripping and retention of an anatomical structure, such clips typically being biased to a closed position, being movable to an open position to receive the anatomical structure and being movable due to the bias from the open position toward the closed position to grasp the anatomical structure. U.S. Pat. No. 4,064,881 to Meredith exemplifies a spring clip particularly useful for ligating the Fallopian tubes. U.S. Pat. Nos. 5,366,458 to Korthoff et al, U.S. Pat. No. 5,342,373 to Stefanchik et al, U.S. Pat. No. 4,961,743 to Kees, Jr. et al, U.S. Pat. No. 4,777,950 to Kees, Jr. and U.S. Pat. No. 4,484,581 to Martin et al are illustrative of spring clips for ligating blood vessels. U. S. Pat. Nos. 4,791,707 to Tucker, U.S. Pat. No. 4,637,395 to Caspar et al, U.S. Pat. No. 4,612,932 to Caspar et al, U.S. Pat. No. 4,396,139 to Hall et al, U.S. Pat. No. 4,217,902 to March, U.S. Pat. No. 3,604,425 to LeRoy, U.S. Pat. No. 3,446,212 to LeRoy and U.S. Pat. No. 3,091,828 to Soltis are representative of spring clips useful in closing incisions or wounds. Many presently available spring clips suffer from various disadvantages. Where the closing force or bias of the spring clips is inadequate, leakage through the anatomical structure held by the spring clips can occur, and the spring clips can move out of position relative to the structure being held. The spring clips are not movable from the closed position to a locked position to further ensure positive gripping and/or retention of the structure being held. Furthermore, many spring clips have complex structure or configurations and/or are larger in size than necessary in order to present structure for being grasped when moving the spring clips from the closed position to the open position. Many conventional spring clips are not capable of being applied in a time efficient and precise manner as is particularly important in endoscopic procedures wherein the size of the operating space and the room for maneuverability are often greatly limited. Additionally, many spring clips are not adaptable for use with clip applicators permitting application of a plurality of spring clips without withdrawal of the applicators from the operative site.

SUMMARY OF THE INVENTION

Accordingly, it is a primary object of the present invention to facilitate occluding, ligating, closing, clamping, grasping, holding, approximating and suturing of anatomical structure or tissue in endoscopic and open surgical procedures.

Another object of the present invention is to provide a multifunctional spring clip for grasping anatomical structure or tissue to occlude, ligate., close, clamp, grasp, hold or approximate the anatomical structure or tissue as well as for grasping a segment of a length of suture material to effect a knot for a stitch formed with the suture material.

A further object of the present invention is to grasp a structure utilizing a spring clip having first and second opposed portions connected to one another and each including an outer segment and an inner segment connected to the outer segment and opposed grasping surfaces carried by the inner segments with the spring clip being biased to a grasping position wherein the grasping surfaces are in contact with one another, being movable to a receiving position wherein the grasping surfaces are moved away from one another to receive the structure therebetween and being movable from the receiving position toward the grasping position due to the bias to grasp the structure between the grasping surfaces.

An additional object of the present invention is to grasp a structure between first and second opposed portions of a spring clip, each opposed portion having an outer segment and an inner segment defining a grasping surface, the first and second opposed portions being connected to one another with the inner segments disposed between the outer segments, the clip being biased to a closed position wherein the grasping surfaces are in contact with one another, being movable, via an opening force applied to the clip, from the closed position to an open position wherein the grasping surfaces are moved away from one another to receive the structure therebetween and being movable from the open position toward the closed position upon removal of the opening force to grasp the structure between the grasping surfaces.

It is also an object of the present invention to grasp a structure between opposed portions of a multifunctional spring clip biased to a grasping position wherein the opposed portions are biased toward one another, movable to a receiving position wherein the opposed portions are moved away from one another to receive the structure therebetween, movable from the receiving position to the grasping position due to the bias to grasp the structure between the opposed portions and movable from the grasping position to a locked position wherein the opposed portions are moved further toward one another.

An additional object of the present invention is to slidably receive a length of filamentous suture material in a passage of a spring clip having means for selectively, fixedly securing the spring clip to a segment of the length of suture material and opposed portions biased toward one another to be normally disposed in a grasping position, being movable away from one another to a receiving position to receive another segment of the length of suture material therebetween and being movable from the receiving position toward the grasping position due to the bias to grasp another segment of the length of suture material to effect a knot for a stitch formed with the suture material.

The present invention also has as an object to apply a spring clip utilizing an applicator having forceps for engaging the spring clip, the spring clip having opposed portions connected with one another and each including an outer segment and an inner segment connected with the outer segment, the clip being biased to a grasping position wherein the inner segments are in contact with one another, being movable from the grasping position to a receiving position wherein the inner segments are moved away from one another to receive a structure therebetween and being movable from the receiving position toward the grasping position to grasp the structure, the forceps being movable from a closed position to an open position to move the clip from the grasping position to the receiving position and from the open position to the closed position to permit the clip to move from the receiving position toward the grasping position.

The present invention has as a further object to apply a spring clip utilizing an applicator including forceps having clip engaging members for engaging the spring clip, the forceps being movable, with the engaging members in an engaged position with the spring clip, from a closed position to an open position to move the clip from a grasping position to a receiving position to receive a structure and from the open position to the closed position to permit the clip to move to the grasping position to grasp the structure, the engaging members being movable from the engaged position to a release position wherein the engaging members are disengaged from the clip to release the clip from the applicator.

Some of the advantages of the present invention are that the multifunctional spring clips can be designed with a bias strong enough to ensure a desired holding force on a structure positioned between the grasping surfaces, enhanced gripping of the structure by the multifunctional spring clips can be achieved with the use of various locking and/or gripping formations, the clips can be made of bioabsorbable or non-bioabsorbable materials, the clips can be applied with the use of applicators capable of being operated in a manner familiar to surgeons, a plurality of clips can be stored in a cartridge removably insertable into the applicators, the distance that the clips extend beyond the forceps of the applicators can be selected in accordance with procedural use and illumination and/or imaging means can be formed integrally, unitarily with the applicators.

These and other objects, benefits and advantages are achieved with the present invention as generally characterized in a multifunctional spring clip including a body having first and second opposed portions and a base connecting the first and second. opposed portions with one another. Each opposed portion includes an inner segment carrying a grasping surface and an outer segment connected to the inner segment, with the inner segments disposed between the outer segments. The clip is biased to a grasping position wherein the grasping surfaces are urged toward one another, is movable from the grasping position to a receiving position wherein the grasping surfaces are moved away from one another to receive a structure therebetween and is movable from the receiving position toward the grasping position due to the bias to grasp the structure between the grasping surfaces. The present invention is further characterized in a clip applicator having forceps for engaging the multifunctional spring clip and movable from a closed position, with the forceps in engagement with the. first and second opposed portions, to an open position to move the clip from the grasping position to the receiving position to receive the structure between the grasping surfaces. The forceps are movable from the open position to the closed position to permit the clip to move from the receiving position toward the grasping position to grasp the structure between the grasping surfaces. The forceps can include clip engaging members for engaging the first and second opposed portions with the clip engaging members being movable between an engaged position wherein the engaging members are in engagement with the first and second opposed portions and a release position wherein the engaging members are disengaged from the first and second opposed portions to release the clip from the applicator. A cartridge storing a plurality of clips is removably insertable in the applicator for selectively advancing one of the clips from the cartridge into engagement with the forceps.

Other objects and advantages of the present invention will become apparent from the following description of the preferred embodiments taken in conjunction with the accompanying drawings, wherein like parts in each of the several figures are identified by the same reference numerals.

BRIEF DESCRIPTION OF THE DRAWINGS

FIG. 4 is a perspective view of the multifunctional clip forming a suturing apparatus with a length of suture material and a needle.

FIG. 5 is a broken side view, partly in section, of the suturing apparatus being used to penetrate anatomical tissue portions from an entry point to an exit point.

FIG. 6 is a broken side view, partly in section, illustrating the segment of suture material extending from the exit point being brought toward the multifunctional clip.

FIG. 7 is a broken side view, partly in section, of the segment being received by the clip to form a stitch.

FIG. 8 is a broken side view, partly in section, illustrating tensioning of the stitch with the clip effecting a knot for the stitch.

FIG. 11 is a broken perspective view of another modification of a multifunctional clip according to the present invention.

FIG. 12 is a side sectional view of the multifunctional clip of FIG. 11 movably secured along two lengths of suture material.

FIG. 13 is a side sectional view of the multifunctional clip of FIG. 11 fixedly secured along the two lengths of suture material.

FIG. 16 is a broken side view, partly in section, of a cartridge for storing a plurality of multifunctional clips according to the present invention.

FIG. 17 is broken side view, partly in section, illustrating a clip being released from the cartridge of FIG. 17.

DESCRIPTION OF THE PREFERRED EMBODIMENTS

The multifunctional clips according to the present invention are particularly useful for performing various procedures or functions in endoscopic and open surgical procedures. For example, the multifunctional clips are useful in grasping or holding anatomical structure to occlude, close, ligate, approximate or clamp the anatomical structure, for example. Accordingly, "anatomical structure" as used herein includes any anatomical or body structure including anatomical organ structure, anatomical tubular structure such as vessels and anatomical tissue. Although the clips are described herein for use in occluding anatomical tubular structure, the clips are useful in many various procedures including procedures to partially or completely occlude various anatomical lumens as well as other artificial or natural anatomical openings or passages as well as to hold, grasp or clamp tissue or approximate tissue for healing, for example. An additional area of use for the multifunctional clips according to the present invention is as a knotting element for the various suturing apparatus and procedures described in applicant's prior applications Ser. No. 08/366, 285 filed Dec. 29, 1994 and Ser. No. 08/377,723 filed Jan. 25, 1995, the disclosures of which are incorporated herein by reference. Accordingly, the multifunctional clips can also be used to secure a first segment of a length of filamentous suture material and to grasp a second segment of the length of suture material to effect a knot for a stitch formed with the suture material. Therefore, as used herein, the "structure" to be grasped by the multifunctional clips according to the present invention includes various anatomical and suture material structure as well as any other structure required to be clamped, held, grasped, occluded, ligated, approximated or closed during endoscopic and open surgical procedures.

Figure 1:
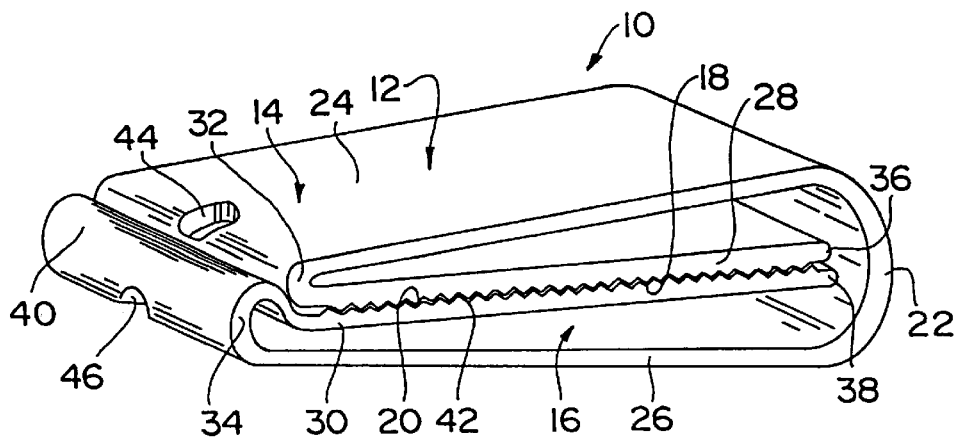
FIG. 1 is a perspective view of a multifunctional clip according to the present invention.

A multifunctional clip according to the present invention is illustrated at 10 in FIG. 1 and includes an integral and unitary body 12 made of any suitable medical-grade material including bioabsorbent and non-bioabsorbent materials. Body 12 is formed or configured to define opposed portions, jaws or legs 14 and 16 having opposed grasping or clamping surfaces 18 and 20, respectively, for grasping a structure such as a blood vessel or a segment of a length of suture material therebetween. Body 12 includes an arcuate base 22 joining legs 14 and 16 to one another and curving about an axis disposed distally of base 22 transverse to and aligned with a longitudinal axis of clip 10. Legs 14 and 16 include outer leg segments 24 and 26, respectively, inner leg segments 28 and 30, respectively, and connecting segments 32 and 34 connecting the outer leg segments with the inner leg segments. Outer leg segments 24 and 26, which are substantially flat or planar, have proximal ends joined to opposing ends of base 22 and distal ends joined to the connecting segments 32 and 34, respectively, which in turn are joined to distal ends of inner leg segments 28 and 30. Each connecting segment is arcuate in configuration and curves about an axis disposed proximally of the connecting segment transverse to the clip longitudinal axis such that the connecting segments 32 and 34 curve in a direction opposite the direction of curvature of base 22. Accordingly, inner leg segments 28 and 30 are disposed between outer leg segments 24 and 26 with opposing ends of each arcuate connecting segment joined to the distal ends of the respective outer and inner leg segments, and the inner and outer segments are disposed in alignment with one another. Inner leg segments 28 and 30 are substantially flat or planar and extend proximally from connecting segments 32 and 34, respectively, to terminate at proximal ends 36 and 38, respectively, adjacent base 22. Inner leg segments 28 and 30 carry or define the opposed grasping surfaces 18 and 20, respectively, for grasping a structure therebetween as explained further below each inner leg segment has an outwardly facing surface facing the outer leg segment to which it is connected and an inwardly facing surface facing opposite the outwardly facing surface. Accordingly, the inwardly facing surfaces face one another and define the grasping surfaces 18 and 20, respectively. Outer leg segment 26 extends distally beyond inner leg segment 30 such that connecting segment 34 is disposed distally of connecting segment 32. Connecting segment 34 forms a curved bump, enlargement or protrusion defining a lip 40 protruding inwardly beyond grasping surface 20 in the direction of the clip longitudinal axis.

Clip 10 is normally biased to a closed, grasping or clamping position wherein grasping surfaces 18 and 20 are urged inwardly toward one another, the grasping surfaces 18 and 20 being disposed in contact with one another with lip 40 at least partially overlapping or extending over connecting segment 32. The clip 10 can be biased in many various ways to be normally disposed in the grasping position and to permit the clip to be moved to an open or receiving position wherein the grasping surfaces are moved outwardly away from one another. One way of biasing clip 10 toward the closed position is by forming clip 10 partially or entirely of resilient, flexible or spring materials; however, the clip can also be biased toward the closed position in many other ways such as with various discrete spring components mounted on or in the body of the clip. In the case of clip 10, body 12 is made of resilient material to bias the opposed portions inwardly toward one another to position the grasping surfaces in contact with one another in the closed position and to permit the outer leg segments to be moved away from one another in the open position with base 22 acting as a hinge.

Clip 10 can include various locking and/or gripping devices, structure or formations for gripping a structure received between the grasping surfaces and/or for locking the clip in the closed position. Clip 10 includes gripping formations in the form of teeth or serrations 42 along grasping surfaces 18 and 20, and such teeth can be complementary, interengaging or non-complementary, non-interengaging. Various other structure and arrangements therefor suitable for locking the opposed portions or legs in the closed position and/or for gripping a structure positioned between the grasping surfaces are disclosed in applicant's aforementioned prior applications incorporated herein by reference.

Notches, indentations, recesses or holes 44 and 46 are formed on or in legs 14 and 16, respectively, for engagement with clip or leg engaging members carried by a forceps of an applicator for clip 10 as described further below. Notches 44 and 46 can be located at any desirable location along legs 14 and 16, respectively, to engage the leg engaging members to allow movement of legs 14 and 16 by the forceps to the open position. In the case of clip 10, notches 44 and 46 are formed at the distal ends of legs 14 and 16. In particular, notches 44 and 46 are disposed along the outer surfaces of connecting segments 32 and 34, respectively; and, depending on the configuration of the clip and the leg engaging members, the notches can extend entirely or partly through the thickness of body 12.

Figure 2:
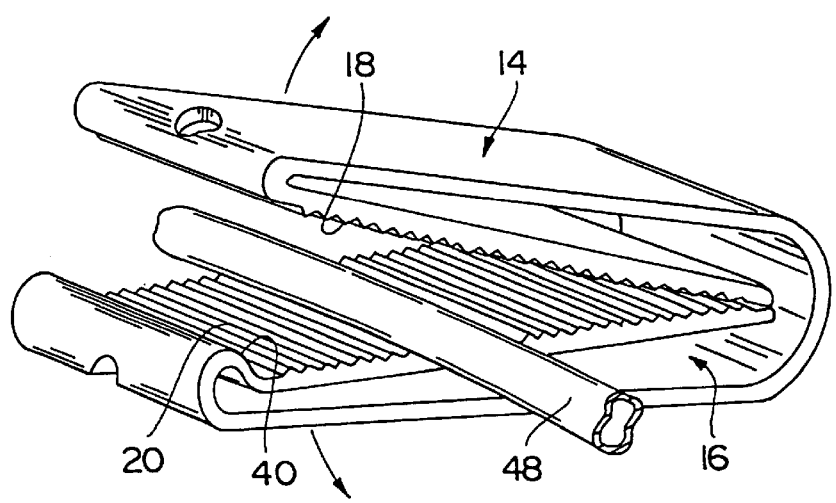
FIG. 2 is a perspective view of the multifunctional clip in a receiving position receiving a blood vessel between grasping surfaces of the clip.
Figure 3:
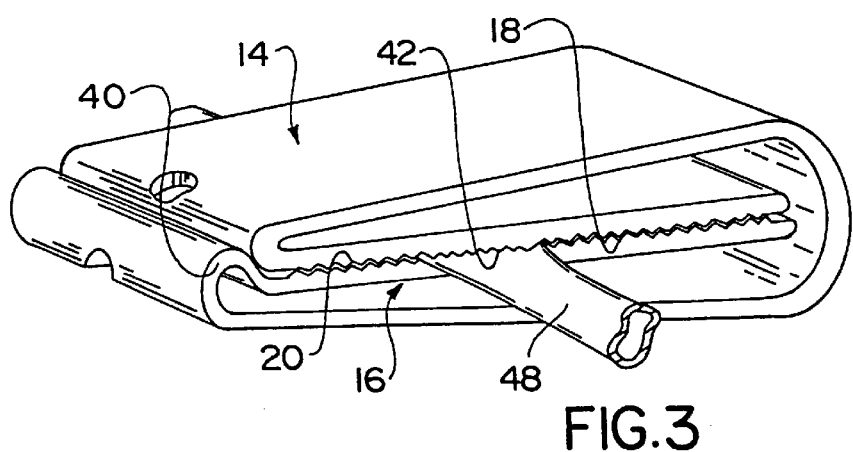
FIG. 3 is a perspective view of the multifunctional clip in a closed position with the blood vessel clamped between the grasping surfaces of the clip.

In use, clip 10 is introduced at an operative site via any suitable instrument, such as a clip applier or applicator for storing and/or applying one or more clips, a preferred applicator for clips 10 being described below. Clip 10 is positioned adjacent a structure, such as blood vessel 48, and is manually or mechanically moved from the normally closed or grasping position shown in FIG. 1 to the open or receiving position illustrated in FIG. 2. An opening force is applied to clip 10 in the direction of the arrows in FIG. 2 to overcome the bias of clip 10 and move the clip to the open position by moving legs 14 and 16 and, therefore, grasping surfaces 18 and 20 away from one another. Once clip 10 has been moved to the receiving position, the clip is positioned on blood vessel 48 with the blood vessel received between grasping surfaces 18 and 20 in a direction transverse to the longitudinal axis of the clip. Upon proper positioning of clip 10 on blood vessel 48, the opening force on clip 10 is removed or released allowing the clip to move toward the closed position due to the bias of the clip. Accordingly, blood vessel 48 will be clamped between the grasping surfaces 18 and 20 with a spring force provided by both opposed portions, and teeth 42 grip the blood vessel as shown in FIG. 3 to prevent displacement of the clip relative to the blood vessel. With clip 10 in the closed or grasping position, lip 40 serves to prevent withdrawal of the blood vessel from the clip and enhances securement of the clip in the closed position.

FIGS. 4–8 illustrate use of clip 10 as a knotting element for a length of suture material as described in applicant's copending patent applications incorporated herein by reference. As shown in FIG. 4, clip 10 is secured to a first segment 50 of a length of filamentous suture material 52 coupled with a needle to form a suturing apparatus. Clip 10 is fixedly secured to the suture material at a grasping site 54 located anywhere along the clip 10. A second segment 56 of the length of suture material is coupled with a needle 58 having a sharp distal end 60 for penetrating anatomical tissue. To suture tissue portions T1 and T2, needle 58 is utilized to penetrate tissue portion T1 at an entry point 62 and is passed through tissue portions T1 and T2 to exit tissue portion T2 at an exit point 64 as shown in FIGS. 5 and 6. The suture material is pulled until clip 10 abuts tissue portion T1 at the entry point 62, and the segment 56 of suture material extending from the exit point 64 is brought back over tissue portions T1 and T2 to the entry point. An opening force is applied to clip 10 to move the clip from the closed position to the open position, and segment 56 is positioned between the grasping surfaces 18 and 20 to form a stitch extending from the clip through the tissue and back to the clip as shown in FIG. 7. The suture material is tensioned to tension the stitch to the extent desired. The opening force on clip 10 is removed or released allowing clip 10 to move toward the closed position such that segment 56 is grasped between the grasping surfaces 18 and 20 to effect a knot for the thusly tensioned stitch as shown in FIG. 8.

Figure 9:
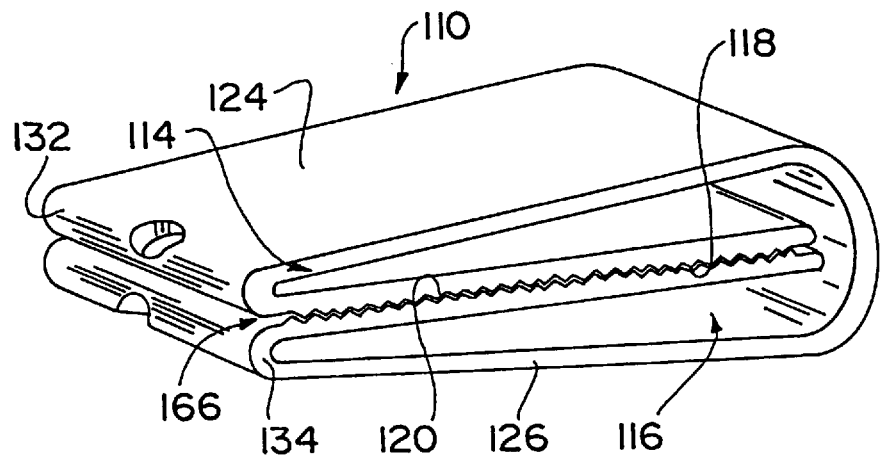
FIG. 9 is a perspective view of a modification of a multifunctional clip according to the present invention.
Figure 10:
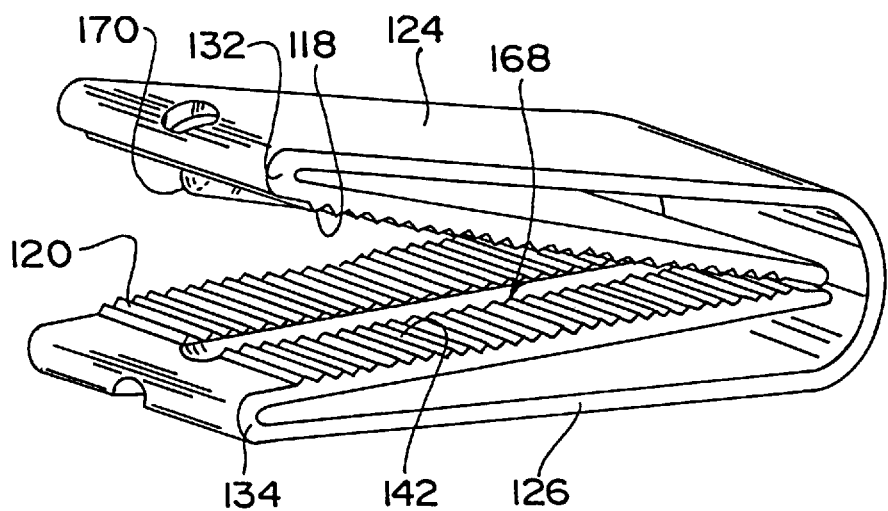
FIG. 10 is a perspective view of the multifunctional clip of FIG. 9 in the receiving position.

A modification of a clip according to the present invention is illustrated at 110 in FIGS. 9 and 10. Clip 110 is essentially the same as clip 10 except that outer leg segments 124 and 126 of clip 110 extend distally the same distance such that connecting segment 134 is aligned with and extends only so far as connecting segment 132. As shown in FIG. 10, clip 110 is provided with additional gripping formations including a groove 168 extending longitudinally along grasping surface 120 and a complementary, corresponding tongue 170 on grasping surface 118 for mating with groove 168.

Use of clip 110 is similar to that previously described in that clip 110 is normally disposed in the closed position with legs 114 and 116 biased inwardly to position grasping surfaces 118 and 120 in contact with one another as shown in FIG. 9 and is moved to an open position to move grasping surfaces 118 and 120 away from one another to receive a structure therebetween as shown in FIG. 10. Once the structure is properly received between the grasping surfaces 118 and 120, the opening force on clip 110 is released causing the clip to move toward the closed position such that the structure will be clamped between the grasping surfaces.

Another modification of a multifunctional clip according to the present invention is illustrated at 210 in FIGS. 11–13. Clip 210 includes a spherical body 212 configured to define opposed partial spherical portions 214 and 216 and an arcuate base 222 joining proximal ends of opposed portions 214 and 216. As best shown in FIG. 12, opposed portions 214 and 216 include curved or partial spherical outer segments 224 and 226, respectively, and planar inner segments 228 and 230, respectively, carrying grasping surfaces 218 and 220. Outer segments 224 and 226 have proximal ends joined to opposing ends of base 222 and have distal ends joined to arcuate connecting segments 232 and 234, respectively, which in turn are joined to distal ends of inner segments 228 and 230. Accordingly, inner segments 228 and 230 are disposed within body 212 with opposing ends of each arcuate connecting segment joined to the distal ends of the respective outer and inner segments. Inner segments 228 and 230 extend proximally from connecting segments 232 and 234, respectively, to retaining members 271 and 273, respectively. Retaining members 271 and 273 include retaining segments 272 and 274, respectively, and ramp segments 276 and 278, respectively. Retaining segments 272 and 274 are carved and extend distally from the proximal ends of inner segments 228 and 230, respectively, along the curved inner surfaces of base 222 and outer segments 224 and 226. Inwardly angled ramp segments 276 and 278 extend distally from retaining segments 270 and 272, respectively, in the direction of inner segments 228 and 230, respectively. The retaining members 271 and 273 are disposed within body 212 and terminate at distal ends, respectively, disposed in contact with the inner segments 228 and 230, respectively, proximally of connecting segments 232 and 234, respectively. Passages 280 and 282 are defined within body 212 between ramp segments 276 and 278 and connecting segments 232 and 234, respectively, the passages extending through body 212 in a direction transverse to a longitudinal axis of clip 210 extending centrally through base 222. Retaining segments 272 and 274 are normally biased to a retaining position wherein an outer or retaining surface 284 of retaining segment 272 is in contact with the inner surface of outer segment 224, and an outer or retaining surface 286 of retaining segment 274 is in contact with the inner surface of outer segment 226. The inner surfaces of outer segments 224 and 226 in contact with retaining segments 272 and 274, respectively, define retaining surfaces cooperating with the retaining surfaces 284 and 286, respectively, to grip a structure therebetween. Teeth 242 are disposed along the retaining surfaces of the retaining segments and the outer segments for enhanced gripping. Retaining segments 272 and 274 are normally disposed in the retaining position and are movable to a non-retaining or receiving position wherein the opposed retaining surfaces are separated or moved away from one another to receive a structure therebetween. The retaining segments can be biased to the retaining position in. many various ways including the use of resilient, flexible or spring materials or discrete spring components. In the case of clip 210, body 212 is formed of resilient material to normally bias the retaining surfaces on retaining segments 272 and 274 in contact with the retaining surfaces on outer segments 224 and 226 and to allow retaining segments 272 and 274 to be moved inwardly toward inner segments 228 and 230, respectively, with ramp segments 276 and 278 flexing to permit such movement. Notches 244 and 246 are disposed along the outer surface of body 212 adjacent the distal ends of opposed portions 214 and 216, respectively, for engaging clip engaging members of a clip applier. Arcuate slots 288 and 290 are formed through the walls of opposed portions 214 and 216, respectively, in communication with passages 280 and 282, the slots 288 and 290 defining tracks along body 212 extending from passages 280 and 282, respectively, to retaining surfaces 284 and 286. Clip 210 is resiliently biased to be normally disposed in the grasping position with grasping surfaces 218 and 220 in contact with one another and is movable to an open position wherein grasping surfaces 218 and 220 are moved away from one another to allow positioning of a structure therebetween.

Use of clip 210 is similar to that previously described; and, where used as a knotting element, one or more lengths of suture material can be passed through passages 280 and 282. As shown for clip 210, two lengths of suture material 252 and 252' extend through passages 280 and 282, respectively; and, with the suture material disposed in passages 280 and 282, the clip 210 will be slidable along the lengths of suture material. Accordingly, the clip 210 will be movably secured to first segments 250 and 250' of the lengths of suture material; and, when it is desired to fix the position of clip 210 along the lengths of suture material, the segments 250 and 250' are manually moved from passages 280 and 282 along ramp segments 276 and 278 via slots 288 and 290 to be forcibly inserted between the retaining surfaces as shown in FIG. 13 wherein the retaining segments are shown flexed or bent to receive the suture material between the retaining surfaces. With the suture material positioned between the retaining surfaces as shown in FIG. 13, the retaining segments 272 and 274 are biased toward the outer segments 224 and 226, respectively, to fixedly secure the suture material therebetween. The lengths of suture material can be utilized to form a stitch, with the clip 210 being moved to the open position to permit second segments 256 and 256' of the lengths of suture material inserted through a contractible loop defined by the lengths of suture material to be positioned between the grasping surfaces 218 and 220 to effect a knot for the stitch as illustrated in FIG. 11 and as disclosed in applicant's prior applications Ser. No. 08/366, 285 filed Dec. 29, 1994 and Ser. No. 08/377,723 filed Jan. 25, 1995 incorporated herein by reference.

Figure 14:
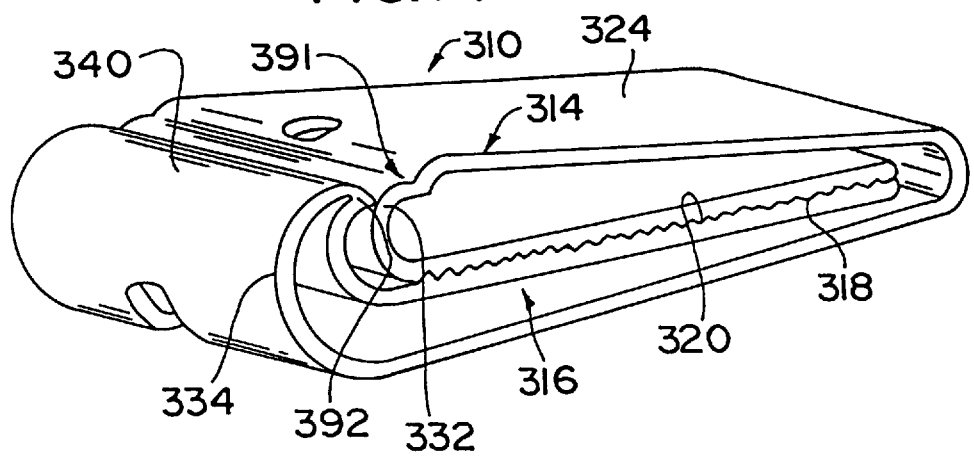
FIG. 14 is a perspective view of a further modification of a multifunctional clip according to the present invention.
Figure 15:
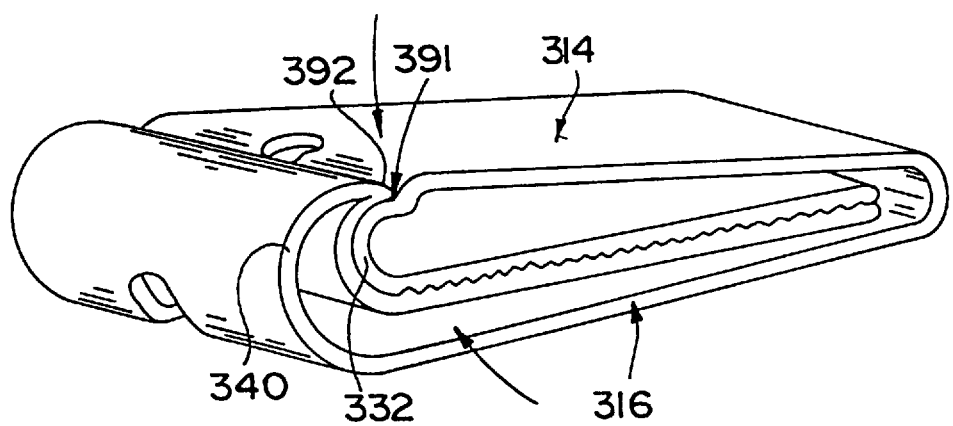
FIG. 15 is a perspective view of the multifunctional clip of FIG. 14 in a locked position.

A further modification of a multifunctional clip according to the present invention is illustrated at 310 in FIG. 14. Multifunctional clip 310 is similar to multifunctional clip 10 except that the multifunctional clip 310 is movable from the normally closed or grasping position to a locked position. Outer leg segment 324 for clip 310 has an inwardly curved distal end joined to connecting segment 332 to define a locking indentation or recess 391 between connecting segment 332 and the outer leg segment 324 transverse to a longitudinal axis of clip 310. Lip 340 for connecting segment 334 curves inwardly toward the locking recess and terminates at a downwardly curved transverse locking finger or detent 392. Clip 310 is normally disposed in the closed position shown in FIG. 14 wherein grasping surfaces 318 and 320 are in contact with one another, and locking finger 392 is disposed out of engagement with locking recess 391, the finger 392 being disposed forwardly of recess 391 in contact with connecting segment 332. The clip 310 is movable to an open position by moving legs 314 and 316 away from one another to create a space for receiving a structure between grasping surfaces 318 and 320. Once the structure is received between the grasping surfaces, the clip is moved toward the closed position upon release of the opening force thereon. Thereafter, legs 314 and 316 are moved inwardly toward one another in the direction of the arrows in FIG. 15 causing locking finger 392 to be moved into the locking recess 391 at which time the clip will be in the locked position with connecting segment 332 compressed against lip 340 and leg 314 held tightly against leg 316. Accordingly, the structure is held by the spring bias of the clip as well as by the locking force provided in the locked position.

The various segments, sections, parts or portions of the multifunctional clips can be of uniform width and thickness or of non-uniform width and/or thickness, and the clips can have various tapered or non-tapered configurations. Various materials can be utilized for the multifunctional clips including various plastics and metals as well as bioabsorbable and non-bioabsorbable materials. Where the multifunctional clips are made of resilient or spring materials, the clips can be made entirely of such materials or partially of such materials so long as the clips are biased or urged toward the closed position and are movable to the open position to receive a structure between the grasping surfaces. The bias force of the clips can be selected in accordance with the structure to be grasped to ensure a desired holding force. With the multifunctional clips according to the present invention, a spring force is provided by both opposed portions for added strength and holding force. The spring force can be provided by the outer segments or both the outer segments and the inner segments in that the outer segments can be biased inwardly toward one another, and the inner segments can be biased inwardly relative to the outer segments. Where the clips are made of bioabsorbable materials, it is desirable that the clips have no sharp edges, corners or small dimensioned pieces which would present areas for ready absorption such that the clips will hold longer without degradation. The clips can be constructed with or without a lip; and, where provided, the lip can overlap the opposite connecting segment partly or entirely and/or can define a lock for locking the clip in a locked position. The multifunctional clips can be 1 designed in many various ways to form or be provided with various locking structure for locking the clips in a locked position wherein the opposed portions or legs are moved further inwardly toward one another from the closed position. Where utilized as knotting elements, the clips can be movable along the suture material or fixed to the suture material, the clip 210 being illustrative of a preferred clip slidable along the suture material.

A cartridge 400 for storing a plurality of multifunctional clips is illustrated in FIG. 16. Cartridge 400 includes an elongate, outer, hollow cylindrical member 401, an elongate, inner tubular member 402 disposed within the outer member 401 and an advancing mechanism 403 for selectively advancing and releasing clips from cartridge 400. Outer member 401 includes an elongate body of hollow or tubular construction terminating proximally at a transverse flange 404 and distally at an inwardly curving or extending distal end 405. Inner member 402 includes an elongate tubular body terminating proximally at a proximal end carrying a removable end cap 406 and distally at a distal end defining a peripheral edge 407. Outer member 401 has an outer diameter or size to be received in a clip applier or applicator as explained further below, and inner member 402 has an outer diameter or size to be closely received within the outer member 401 via an opening in flange 404 while allowing longitudinal movement of the outer and inner members relative to one another. A handle is disposed at the proximal end of cartridge 400 and includes opposed, bi-lateral, U-shaped handle members 408 and 408' defining opposed distal hand grips 409 and 409' connected with flange 404, and opposed proximal hand grips 411 and 411' connected with a transverse flange 413 at the proximal end of inner member 402. Handle members 408 and 408" are made of resilient or spring material or designed in a manner to normally position the inner and outer members relative to one another such that the inner member distal end is disposed proximally of the outer member distal end and the inner member proximal end is disposed proximally of the outer member proximal end as shown in FIG. 16. A plurality of serially arranged multifunctional clips 10 are disposed in inner member 402 in end-to-end relationship. The clips 10 are biased or urged distally by advancing mechanism 403 including a spring 415 mounted in compression between end cap 406 and a cylindrical push member 417 having a curved or concave distal wall biased into abutment with the base 22' of the most proximal clip 10'. The outer member distal end 405 is flexible, resilient, made of spring material or otherwise biased to extend inwardly in the direction of a longitudinal axis of cartridge 400 with a force greater than the distal bias on clips 10. Accordingly, distal end 405 presents an obstruction normally disposed in the path of clips 10 to prevent release of clips 10 from cartridge 400 due to the bias of spring 415.

When it is desired to advance a clip distally for release from cartridge 400, the handle is squeezed or compressed causing relative movement of the outer member 401 and/or the inner member 402. Relative movement of the outer and/or inner members via operation of the handle overcomes the bias of distal end 405 such that the distal end 405 is moved outwardly or spread by peripheral edge 407 an amount sufficient to allow spring 415 to advance the distal-most clip 10" from cartridge 400 as shown in FIG. 17. Upon release of the cartridge handle, relative movement of the outer and/or inner members causes the peripheral edge 407 to again be positioned proximally of distal end 405 preventing release of the next clip.

Figure 18:
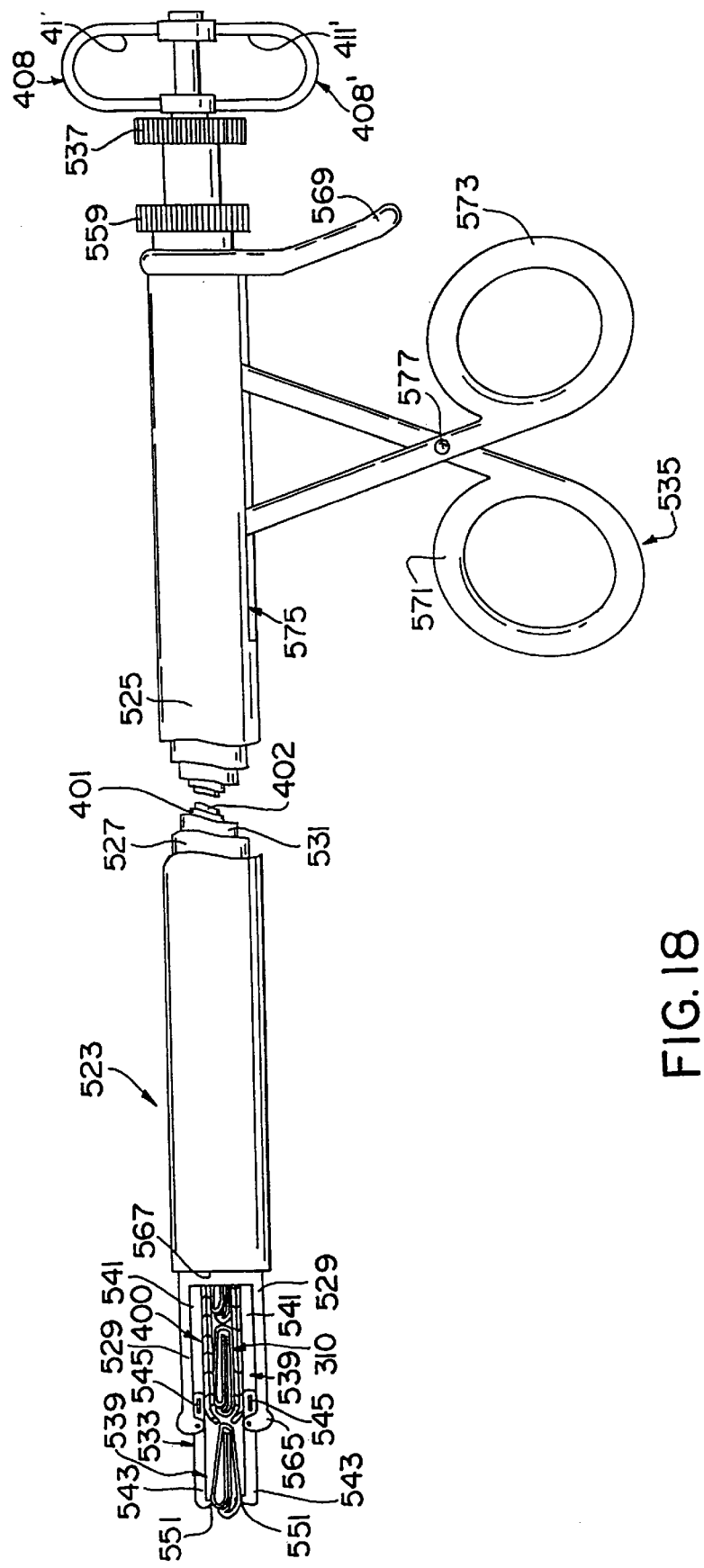
FIG. 18 is a broken side view, partly in section, of a clip applicator according to the present invention.
Figure 19:
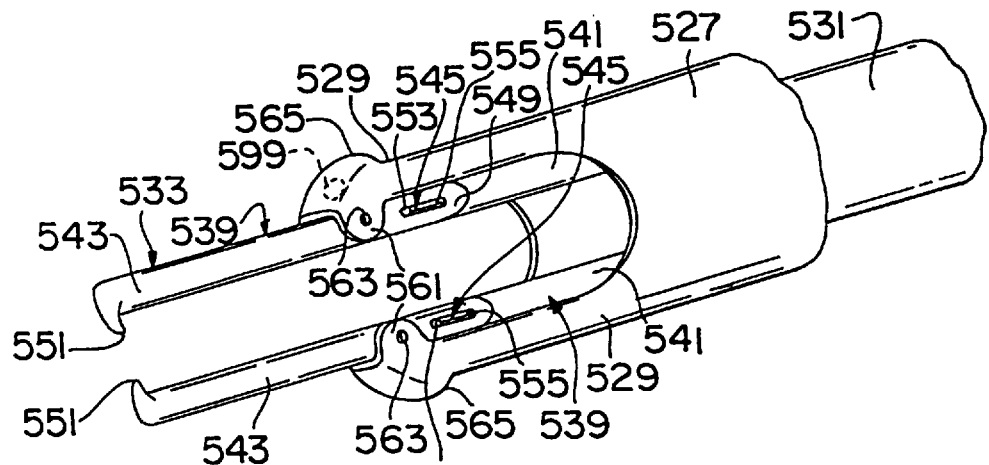
FIG. 19 is a broken perspective view of a distal end of the clip applicator.
Figure 20:
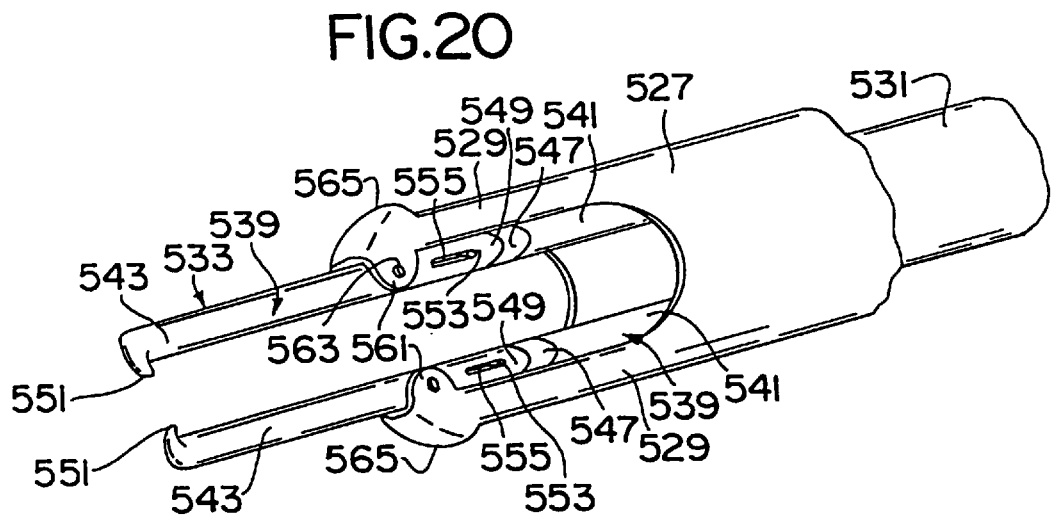
FIG. 20 is a broken perspective view of the distal end of the clip applicator illustrating movement of the clip engaging members from the engaged position to the release position.
Figure 21:
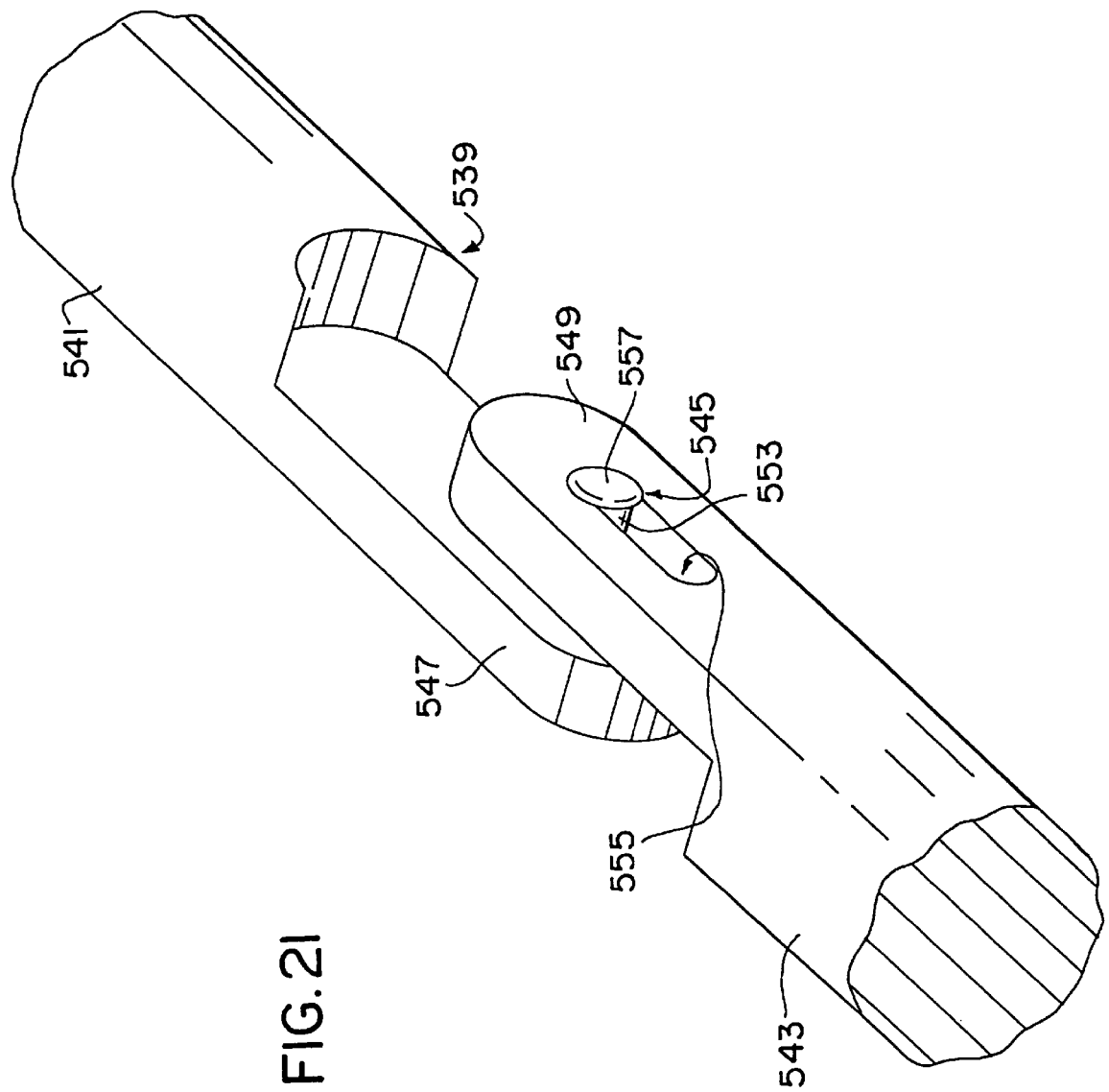
FIG. 21 is a broken perspective view of a joint connecting the distal forceps arm portions to proximal forceps arm portions of the forceps of the clip applicator.

A clip applicator or applier for use with the multifunctional clips according to the present invention is illustrated in FIG. 18 wherein the clip applicator 523 is shown loaded with a clip cartridge 400 storing a plurality of multifunctional clips 310. Clip applicator 523 includes an outer elongate tubular member 525, a middle elongate tubular member 527 received in outer member 525 and carrying arms 529, an inner elongate tubular member 531 received in middle member 527 and carrying forceps 533 and a handle 535 at a proximal end of the applicator. Inner member 531 includes an elongate tubular body terminating proximally at a collar 537 and distally at forceps 533 with the inner member body having an internal diameter or size to receive outer member 401 of cartridge 400. As best shown in FIGS. 19 and 20, wherein outer member 525 is not shown, forceps 533 includes a pair of opposed forceps arms 539, each of which includes a proximal forceps arm portion 541 and a distal forceps arm portion 543 connected to the proximal forceps arm portion 541 by a joint 545. Each proximal forceps arm portion 541 has a proximal end connected with a distal end of the inner member body and a distal end of reduced width forming a protruding ear 547 as shown in FIG. 21. Each distal forceps arm portion 543 has a proximal end of reduced width forming a protruding ear 549 corresponding to ears 547 and a distal end provided with or forming a clip or leg engaging member 551. Each joint 545, as best shown in FIG. 21, is formed by a pin 553 protruding from ear 547 in a transverse direction and a longitudinal slot 555 in ear 549 for receiving pin 553 when ears 547 and 549 are disposed in overlapping relation. The pins 553 are movable along the slots 555 and are held therein by enlarged ends 557 of the pins with the ears 549 confined between ears 547 and enlarged ends 557. Although the forceps arms are shown as having a round configuration in cross-section and the ears are shown as having a rectangular configuration in cross-section, it should be appreciated that the forceps arms and ears can have any desirable configuration. Clip engaging members 551 are formed integrally, unitarily with distal forceps arm portions 543 and have a configuration defining inwardly protruding hooks for engagement with the notches of clips 310. It should be appreciated, however, that the clip engaging members can be formed separately from the distal forceps arms portions and can have various other configurations or structure to engage or hold the legs or opposed portions of the multifunctional clips, with or without the use of notches, for movement to the receiving position in response to opening of the forceps. Additionally, various other structure useful in the procedure to be performed can extend distally beyond the distal forceps arm portions including additional forceps members or hook members for grasping tissue, for example. Forceps 533 is formed of resilient, flexible or spring materials such that the forceps arms 539 are normally biased outwardly from the inner member body in a direction away from the applicator longitudinal axis to be normally disposed in an open position. However, the forceps 533 can be normally biased or urged toward the open position in many various ways including with the use of discrete spring components.

Middle member 527 includes an elongate tubular body receiving the elongate body of inner member 531 while allowing relative movement of the inner and middle members. The middle member body terminates proximally at a collar 559 and distally at opposed arms 529. Each arm 529 has a proximal end connected with the middle member body and a distal end forming spaced, parallel flanges 561 extending or protruding inwardly from arm 529 in the direction of the clip applier longitudinal axis. Arms 529 extend distally from the middle member body to receive distal forceps arm portions 543 between flanges 561. Arms 529 are connected to forceps arms 539 at joints 563 disposed distally of joints 545 and including pins extending between the flanges 561 and through the distal forceps arm portions 543. Arms 529 maintain forceps 533 in a closed or initial position prior to use and can bend, pivot or buckle outwardly of the middle member body in a direction away from the clip applier longitudinal axis when the forceps are moved to an open position as explained further below. A bump, protrusion or abutment 565 is disposed on each arm 529 to be disposed in the path of outer member 525 when the outer member is moved distally relative to middle member 527 as explained further below.

Outer member 525 has a distal end terminating at a peripheral edge 567 and a proximal end terminating at a depending finger grip 569. Handle 535 includes a pair of pivotally connected hand grips 571 and 573 having or forming finger receiving holes at lower ends thereof. The lower end of hand grip 571 is disposed distally of the lower end of hand grip 573 with the hand grips arranged to cross over one another such that an upper end of hand grip 571 is disposed proximally of an upper end of hand grip 573. The upper end of hand grip 573 is connected to the middle member 527 with the upper end of the hand grip 573 extending through a longitudinal slot 575 in outer member 525. The upper end of hand grip 571 is connected to the inner member 531 with the upper end of hand grip 571 extending through slot 575 and through a longitudinal slot (not shown) in middle member 527. The hand grips 571 and 573 are pivotally connected to one another at a joint, pivot or pin 577 at the location where the hand grips cross over one another. Joint 577 can be provided with a member, such as a torsion spring (not shown), for normally biasing the hand grips 571 and 573 to maintain the clip applier in an initial position.

Figure 22:
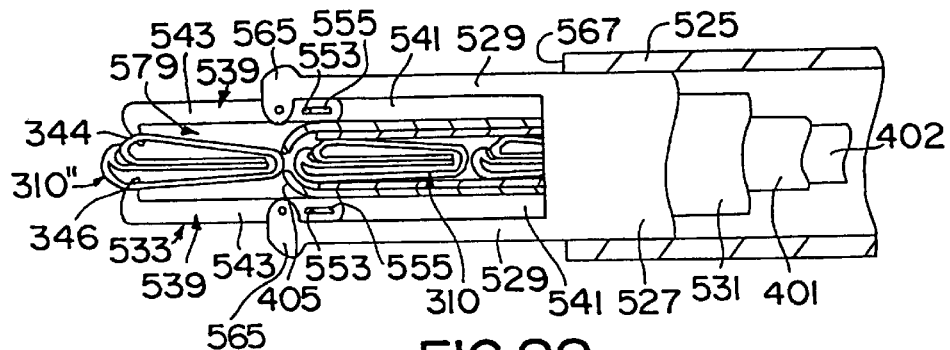
FIG. 22 is a broken side view, partly in section, illustrating the clip applicator in an initial position with the forceps engaging a clip released from a cartridge inserted in the applicator.

In the initial position, handle 535 positions the inner and middle members relative to one another such that arms 529 are disposed parallel or substantially parallel with the clip applier longitudinal axis to constrain or maintain the forceps arms 539 in a closed position wherein the engaging members 551 are in a position ready to engage a clip 310 released from clip cartridge 400 as shown in FIGS. 18 and 22. In the closed position, the proximal forceps arm portions 541 are aligned with the distal forceps arm portions 543 to extend parallel or substantially parallel with the clip applier longitudinal axis with pins 553 disposed at distal or forward ends of slots 555. Distal forceps arm portions 543 are constrained against movement in the proximal direction by proximal forward arm portions 541 in abutment with ears 549 and in the distal direction by the arms 529. In the initial position, the peripheral edge 567 of outer member 525 is disposed proximally of abutments 565 as shown in FIG. 22. The outer member finger grip 569 is disposed proximally of handle 535, and the outer member can be maintained in the initial position in many various ways, such as with a friction fit with the middle member or with a spring bias, for example, while allowing the outer member to be moved longitudinally relative to the middle member as permitted by slot 575. In the case of clip applicator 523, the position of the outer member is maintained by a friction fit capable of being overcome by a force applied to the outer member via the finger grip 569. The middle member collar 559 is disposed proximally of finger grip 569 and distally of inner member collar 537. The collars 559 and 537 can be knurled for enhanced gripping to permit rotation of the middle member and/or the inner member to selectively change or adjust the position or orientation of forceps 533. It should be appreciated that the middle and inner members can be mounted to handle 535 in many various ways to be non-rotatable or to be rotatable such as by being rotatably mounted in collars or sleeves at the upper ends of the hand grips 571 and 573, for example.

Prior to use, clip applier 523 is loaded with cartridge 400 inserted in the inner member 531 with the cartridge handle in abutment with collar 537, and the cartridge can be retained in the applicator in many various ways including a friction fit. The distal end 405 of cartridge outer member 401 will be disposed proximally of the distal end of forceps 533 such that a space 579 is defined between the forceps arms to receive a clip 310 released from cartridge 400. The clip applicator 523 will be in the initial position with forceps 533 maintained in the closed position with leg engaging members 551 a position ready to engage a clip 310 released from cartridge 400; and, in the initial position, the distal forceps arm portions 543 will be constrained from moving proximally and distally.

When it is desired to apply a clip 310 to a structure, the cartridge handle is compressed, such as via finger pressure against proximal hand grips 411 and 411' using the thumb of the hand grasping the applicator handle 535. Accordingly, the cartridge inner member 402 will be moved distally relative to the cartridge outer member 401 to move distal end 405 outwardly to release or eject the distalmost clip 310" from the cartridge 400 into the space 579. The distalmost clip 310", upon release from cartridge 400, will be positioned in engagement with the leg engaging members 551 to be held by forceps 533. As shown in FIG. 22, leg engaging members 551 will be in an engaged position wherein the leg engaging members 551 are received or engaged in notches 344 and 346 of clip 310", and the clip 310" held by forceps 533 will prevent release of the next clip from cartridge 400. Upon release of the cartridge handle, the cartridge inner member 402 will be moved proximally. relative to the cartridge outer member 401 due to the bias of the cartridge handle, thusly preventing release of the next clip.

Figure 23:
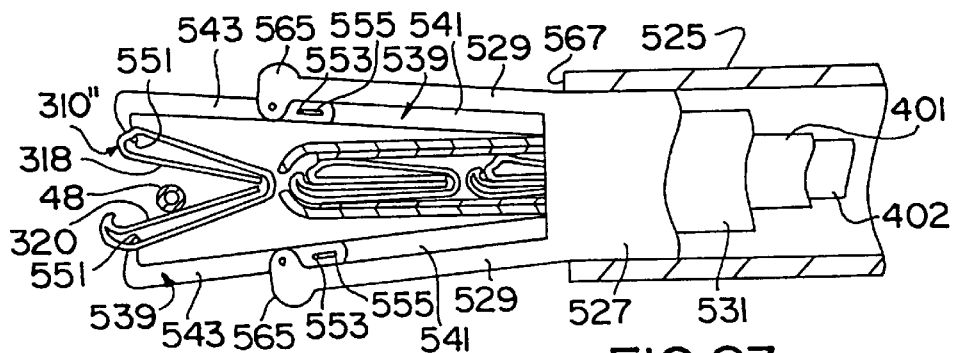
FIG. 23 is a broken side view, partly in section, showing the forceps in an open position to move the clip from the grasping position to the receiving position.
Figure 24:
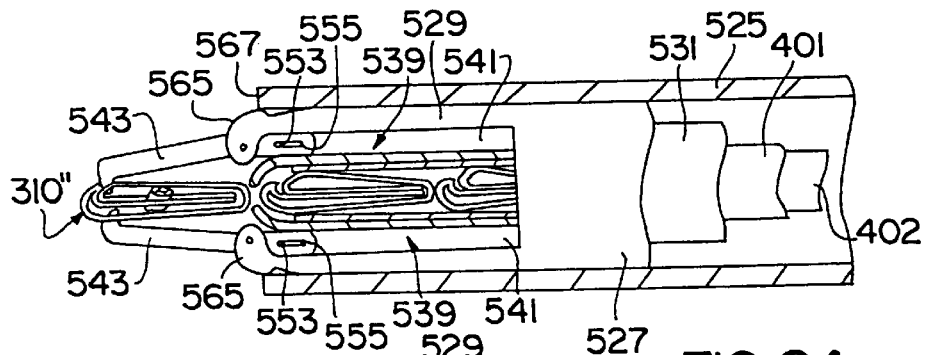
FIG. 24 is a broken side view, partly in section, showing the forceps moved inwardly from the closed position to move the clip from the grasping position to a locked position.
Figure 25:
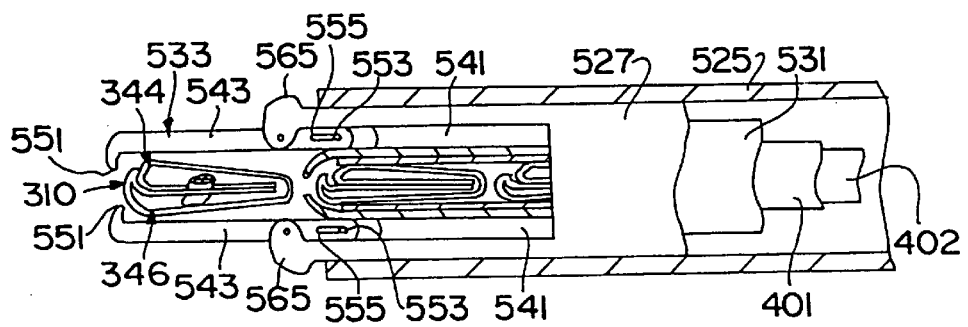
FIG. 25 is a broken side view, partly in section, illustrating movement of the clip engaging members to the release position to disengage the clip from the forceps.

To open the clip 310" held by forceps 533, the applicator handle 535 is squeezed causing the middle member 527 to be moved proximally and the inner member 531 to be moved distally. Relative movement of the middle and inner members via squeezing of handle 535 causes the forceps arms 539 to be moved to the open position due to the spring bias of forceps 533 and due to the mechanical force provided by arms 529 pivoting outwardly of the middle member body as shown in FIG. 23. Accordingly, the forceps 533 will be held in the open position with both a spring force and a mechanical force such that clip 310″ held thereby is moved from the normally closed position to the open position with pins 553 remaining at the forward ends of slots 555. With the clip 310″ held open by clip applier 523, a structure such as blood vessel 48 is positioned between the grasping surfaces 318 and 320, and the handle 535 is released with the force or bias provided thereby causing the clip applier to return to the initial position at which time clip 310″ will be moved toward the closed position to clamp blood vessel 48. Once the clip applier 523 has been returned to the initial position, outer member 525 is moved distally relative to middle member 527 via a manual force applied to finger grip 569. Movement of outer member 525 distally causes peripheral edge 567 to engage abutments 565 thereby compressing forceps 533 causing forceps arms 539 to pivot or move inwardly in the direction of the clip applier longitudinal axis to compress clip 310″ and move the clip 310″ from the closed position to the locked position. As shown in FIG. 24, outer member 525 in engagement with abutments 565 causes the distal forceps arm portions 543 to bend or pivot inwardly to move clip 310″ to the locked position. The clip applier handle 535 is then spread, as permitted by the slots in the outer and middle members, by moving the lower ends of hand grips 571 and 573 away from one another causing the middle member 527 to be moved distally and the inner member 531 to be moved proximally. Movement of middle member 527 distally and inner member 531 proximally via spreading operation of handle 535 causes the distal forceps arm portion 543 to be moved longitudinally, distally with pins 553 moving toward proximal or rearward ends of slots 555. Movement of distal forceps arm portions 543 distally along with the middle member 527 causes the engaging members 551 to be moved distally or forwardly out of notches 344 and 346 to a disengaged or release position thusly releasing the clip 310″ from the forceps 533. Movement of middle member 527 distally causes abutments 565 to be moved out of engagement with outer member 525 such that the forceps arms 539 are moved outwardly in the disengaged position to further facilitate removal of the clip 310″ from the clip applier. The clip applier 523 is then moved laterally or sideways relative to the clip 310″, which remains in place on the blood vessel 48. Upon release of handle 535 and movement of outer member 525 proximally, the clip applier will be in the initial position ready for use to apply the next clip without withdrawal of the clip applier from the body.

The clip applier can be designed in many various ways to open the multifunctional clips to receive a structure between the grasping surfaces. The forceps of the clip applier can have various structure or configurations for engaging or holding the multifunctional clips to move the clips from the closed position to the open position. Where clip engaging members are used, the engaging members can be provided on the clip applier for engaging structure such as notches on the clips as described herein or the engaging members can be provided on the clips themselves for engaging structure such as notches on the clip applier. The clip applier handle can have various configurations and can be provided with various locking structure such as ratchet mechanisms for locking the handle in the compressed and/or spread positions. Where the multifunctional clips do not have a locked position, the clip applier can be designed without the outer member 525. The inner and middle members can be designed or arranged in many various ways such that the forceps is maintained in the closed position when the clip applier is in the initial position and is moved to the open position when the inner and/or middle member is moved relative to the other of the inner and/or middle member. For example, the middle member arms can be designed with sufficient strength to maintain the forceps in the closed position and/or the forceps can be maintained in the closed position by being partially disposed within the middle member body in the initial position. The clips can be released or disengaged from the clip applier in many various ways in addition to those shown and described herein. For example, the cartridge can be mounted for proximal movement relative to the clip applier allowing the cartridge to be moved back so that a space is created within the forceps between the clip held thereby and the distal end of the cartridge permitting the clip applier to be moved distally relative to the clip to disengage the clip from the forceps. As another example, the distal ends of the forceps arms can be pivotable, rotatable or hinged for outward movement to disengage the forceps from the clip as effected by tethers, control wires or the like connected with the forceps arms distal ends and operable from a proximal end of the clip applier. As a further example, the clips can be designed to automatically release or disengage the forceps therefrom in response to movement of the clips further inwardly from the closed position. Various additional instruments including graspers can be utilized to grasp and/or manipulate the clips within the forceps to accomplish and/or facilitate disengagement and/or removal of the clips from the forceps. Illumination means and/or imaging means including fiber optic cables, imaging chips such as CCD chips, and lenses can be disposed in the walls of any one or more of the members forming the clip applier. For example, fiber optic illumination means 599 shown in dotted lines in FIG. 19 extends through the wall thickness of middle member 527 including arm 529 to be formed integrally, unitarily with the middle member.

Figure 26:
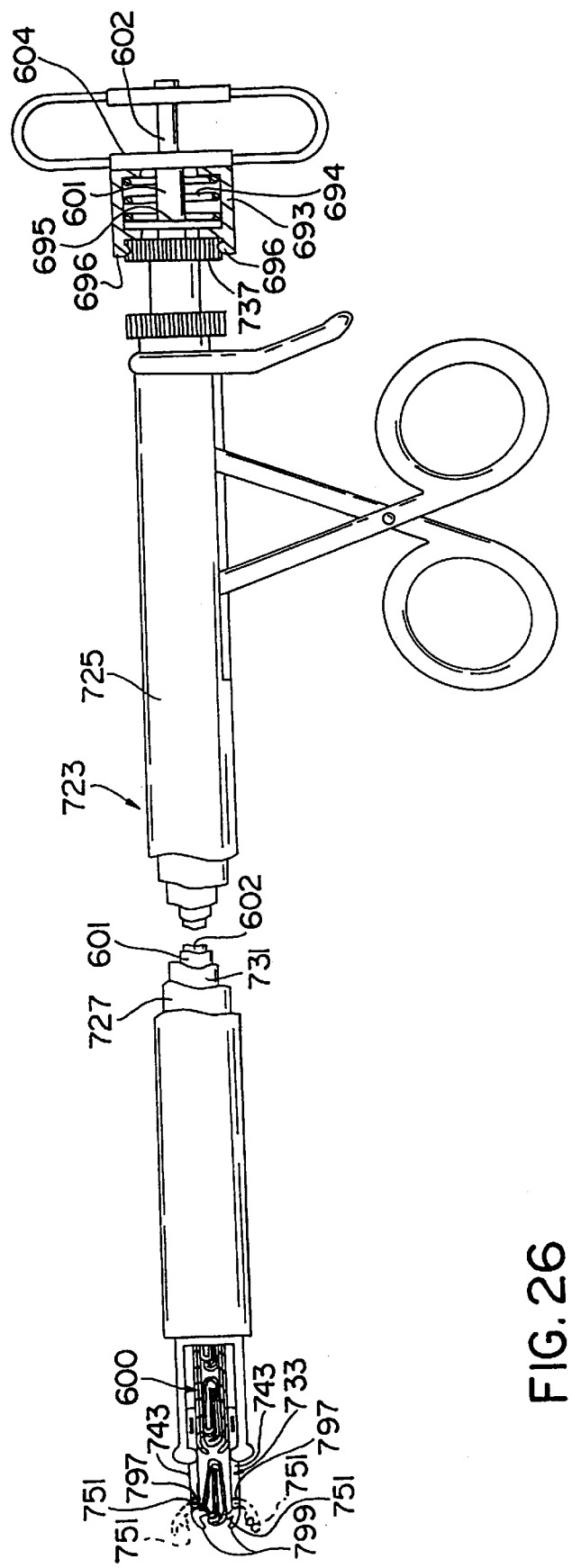
FIG. 26 is a broken side view, partly in section, of a modification of a clip applier according to the present invention.

A modification of a cartridge and a clip applier according to the present invention are illustrated at 600 and 723, respectively, in FIG. 26. Cartridge 600 is similar to cartridge 400 except that cartridge 600 is spring biased to permit movement of cartridge 600 proximally relative to clip applicator 723. Cartridge 600 includes a cylindrical housing 693 disposed distally of flange 604 with the cartridge outer member 601 slidably passing through aligned openings in forward and rearward walls of the housing. A helical coil spring 694 is disposed concentrically around outer member 601 to be disposed in housing 693 between the housing rear wall and a flange 695 secured to outer member 601. Spring 694 is mounted in compression to bias the housing rear wall in abutment with flange 604 and flange 695 in abutment with the housing forward wall in a rest position for cartridge 600. The cartridge 600 is inserted in the inner member 731 of clip applier 723, and the housing 693 has detents 696 for engaging collar 737 of inner member 731 to secure the housing to the clip applier. Accordingly, when the cartridge is manually moved or pulled proximally, flange 695 will be moved proximally in housing 693 against the bias of spring 694 such that the cartridge 600 will be moved proximally relative to the clip applier 723 to create a space within forceps 733 between the distal end of the cartridge and a clip held by the forceps. When the cartridge is released, spring 694 will move the cartridge distally causing flange 695 to abut the forward wall of housing 693 thusly returning the cartridge to the rest position. Although the cartridge 600 is shown as being movable proximally from a rest position relative to the clip applicator, it should be appreciated that the cartridge can be designed for both proximal and distal movements from the rest position.

The clip applier 723 is similar to clip applier 523 except that the clip engaging members 751 of forceps 733 are formed separately from the distal forceps arm portions 743 and are connected to the distal forceps arm portions 743 by spring joints, pivots or hinges 797. The clip engaging members 751 are thus pivotally or hingedly mounted to the distal forceps arm portions 543 to be movable between the engaged position wherein the clip engaging members are positioned to engage a clip released from cartridge 600 and a disengaged or release position wherein the engaging members are moved outwardly in a direction away from a longitudinal axis of clip applier 723 to disengage or release a clip from forceps 733 as shown in dotted lines. The engaging members 751 can be moved between the engaging and release positions in many various ways such as with the use of tethers, control wires or strings connected with the engaging members and extending along the clip applicator to control wheels at a proximal end of the clip applicator. Forceps 733 includes additional forceps arms or hook-like members 799 extending from or disposed distally of the engaging members 751 for use in grasping or manipulating anatomical structure or for other uses.

Use of cartridge 600 and clip applier 723 is similar to that previously described. Cartridge 600 can be moved proximally relative to the clip applier 723 subsequent to closure of a clip to grasp a structure positioned between the grasping surfaces thereof. Accordingly, the cartridge 600 can be moved back to create a space within forceps 733 allowing the clip applier 723 to be moved distally or forwardly to move the engaging members from the engaged position to the release position to disengage the engaging members 751 from the notches in the clip held by forceps 733. The clip applier 723 can then be moved laterally or sideways to remove forceps 733 from the clip which remains in place on the structure. Alternatively or additionally, the engaging members 751 can be moved from the engaged position holding the clip in forceps 733 to the disengaged or release position wherein the engaging members are pivoted or moved outwardly to release the engaging members from the clip as shown in dotted lines.

Figure 27:
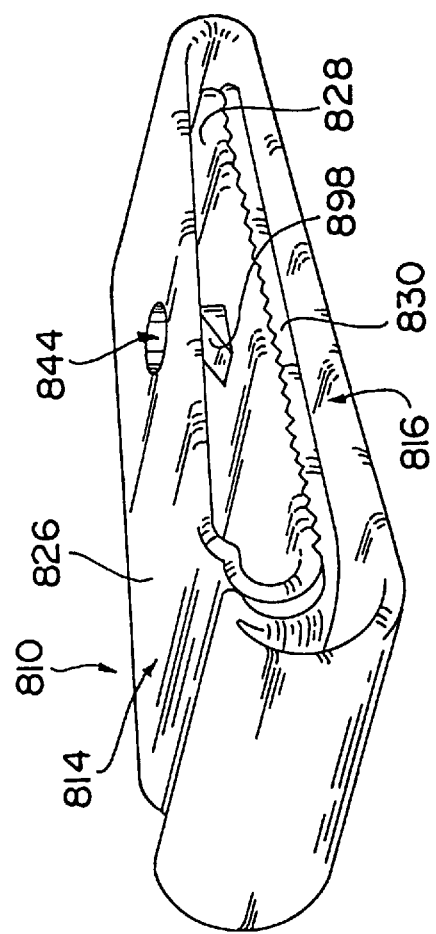
FIG. 27 is a perspective view of a further modification of a multifunctional clip according to the present invention.

Another modification of a multifunctional clip according to the present invention is illustrated at 810 in FIG. 27. Multifunctional clip 810 is similar to multifunctional clip 310 except that multifunctional clip 810 has holes positioned proximally along legs 814 and 816 for engaging the clip engaging members of a clip applier. Clip 810 is made of bioabsorbable materials and has rounded edges. A hole 844 is formed in outer leg segment 824, and a corresponding hole (not shown) is formed in outer leg segment 826. A cam surface 898 including an angled protrusion is disposed on an outer surface or face of inner leg segment 828, and a corresponding cam surface (not shown) is disposed on an outer surface of inner leg segment 830. The holes are aligned with the cam surfaces and are spaced from the cam surfaces when the clip 810 is in the closed or grasping position as shown in FIG. 27.

Figure 28:
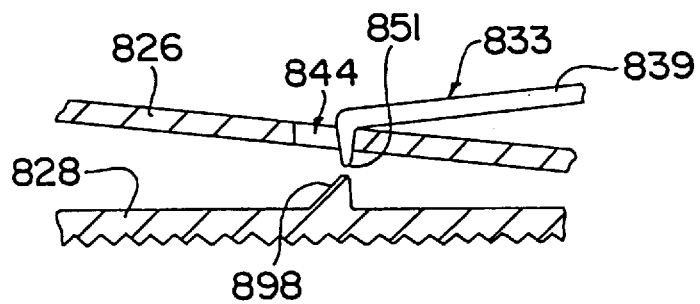
FIG. 28 is a broken, side sectional view showing a clip engaging member of a forceps engaged with the multifunctional clip of FIG. 27.
Figure 29:
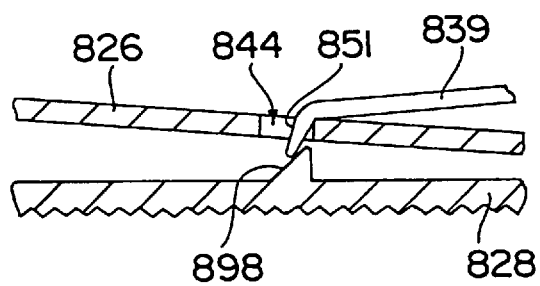
FIG. 29 is a broken, side sectional view illustrating the multifunctional clip of FIG. 27 being moved from a grasping position to the locked position.
Figure 30:
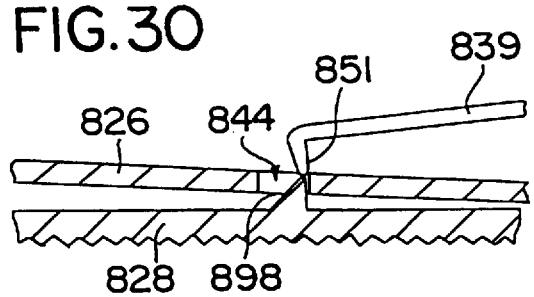
FIG. 30 is a broken, side sectional view showing the clip engaging member being moved to the release position in response to movement of the clip to the locked position.

Use of clip 810 is similar to that described above for clip 310 except that movement of clip 810 further inwardly from the closed position by forceps 833 causes the clip engaging members of the forceps to be moved from the engaged position to the release position for disengagement from the holes. FIG. 28 illustrates arm 839 of forceps 833 in the engaged position with leg engaging member 851 received in hole 844 with the clip in a closed position, and it should be appreciated that a similar forceps arm will be engaged with the hole in the opposed outer leg segment. When arm 839 is moved or pivoted inwardly to move clip 810 from the closed position to the locked position as shown in FIG. 29, leg engaging member 851 will contact cam surface 898, and the leg engaging member 851 can be made to flex or bend due to contact with the cam surface. Upon arm 839 moving the leg segment 824 inwardly to the locked position, cam surface 898 causes the leg engaging member 851 to be moved out of hole 844 to the release position disengaging or releasing clip 810 from forceps 833, and the angled protrusion can move into hole 844.

It should be appreciated from the above that the forceps can engage the clips anywhere along the bodies of the clips. Where the forceps engage the multifunctional clips proximally of the distal ends of the clips, the forceps will not interfere with structure that may be present at the operative site. Accordingly, the extent to which the clips extend or protrude distally beyond the distal end of the applicators can be selected in accordance with procedural use to facilitate positioning or application of the clips at an operative site as is especially important where the operative site provides minimal or limited room or access.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A multifunctional clip for use in endoscopic and open operative procedures comprising a body having first and second opposed portions and a base connecting said first and second opposed portions, said first opposed portion including a first outer segment having a proximal end connected to said base and having a distal end, a first inner segment having a distal end connected to said distal end of said first outer segment and extending proximally toward said base, said second opposed portion including a second outer segment having a proximal end connected to said base and having a distal end, a second inner segment having a distal end connected to said distal end of said second outer segment and extending proximally toward said base such that each of said inner segments is disposed between said outer segments, said first inner segment having a first outwardly facing surface facing said first outer segment and a first inwardly facing surface opposite said first outwardly facing surface, said second inner segment having a second outwardly facing surface facing said second outer segment and a second inwardly facing surface facing said first inwardly facing surface such that said first and second inwardly facing surfaces define first and second grasping surfaces, respectively, for grasping a structure therebetween, at least one of said opposed portions having a retaining member extending distally from a proximal end of said inner segment of said at least one opposed portion, said retaining member having a retaining segment in contact with said outer segment of said at least one opposed portion and a ramp segment extending from said retaining segment to an end in contact with said outwardly facing surface of said at least one opposed portion such that a passage for slidably receiving a structure is defined in said at least one opposed portion distally of said ramp segment, said retaining segment being movable away from said outer segment of said at least one opposed portion to receive the structure from said passage between said retaining segment and said outer segment of said at least one opposed portion, said retaining segment being movable toward said outer segment of said at least one opposed portion to fixedly grasp the structure between said retaining segment and said outer segment of said at least one opposed portion.

2. A multifunctional clip as recited in claim 1 wherein said retaining segment is biased into contact with said outer segment of said at least one opposed portion.

3. A multifunctional clip as recited in claim 2 wherein said first and second outer segments include inwardly facing surfaces facing said first and second outwardly facing surfaces, respectively, and said retaining segment is biased into contact with said inwardly facing surface of said outer segment of said at least one opposed portion.

4. A multifunctional clip as recited in claim 3 and further including gripping formations on said retaining segment and said inwardly facing surface of said outer segment of said at least one opposed portion for gripping the structure between said retaining segment and said outer segment of said at least one opposed portion.

5. A multifunctional clip as recited in claim 4 wherein said retaining segment includes an outwardly facing surface facing said inwardly facing surface of said outer segment of said at least one opposed portion and said gripping formations are disposed on said outwardly facing surface of said retaining segment.

6. A multifunctional clip as recited in claim 5 wherein said first opposed portion includes a first one of said retaining members and said second opposed portion includes a second one of said retaining members.

7. A multifunctional clip as recited in claim 5 wherein said clip is biased to a grasping position wherein said first and second grasping surfaces are urged toward one another, is movable to a receiving position wherein said first and second grasping surfaces are moved away from one another to receive a structure therebetween and is movable from said receiving position toward said grasping position to grasp the structure between said first and second grasping surfaces.

8. A multifunctional clip as recited in claim 7 wherein said first and second grasping surfaces are biased into contact with one another in said grasping position.

9. A multifunctional clip for use in endoscopic and open operative procedures comprising
a spherical body having partial spherical first and second opposed portions connected to one another at proximal ends of said first and second opposed portions, said first opposed portion including a partial spherical first outer segment, a planar first inner segment extending from a distal end of said first outer segment toward said proximal end of said first opposed portion, said second opposed portion including a partial spherical second outer segment, a planar second inner segment extending from a distal end of said second outer segment toward said proximal end of said second opposed portion such that said first and second inner segments are disposed within said spherical body, said first inner segment having a first outwardly facing surface facing said first outer segment and a first inwardly facing surface facing said second inner segment, said second inner segment having a second outwardly facing surface facing said second outer segment and a second inwardly facing surface facing said first inwardly facing surface such that said first and second inwardly facing surfaces define first and second grasping surfaces, respectively, for grasping a structure therebetween, at least one of said opposed portions having a curved retaining segment extending distally from a proximal end of said inner segment of said at least one opposed portion and a planar ramp segment extending angularly, distally from a distal end of said retaining segment toward said outwardly facing surface of said at least one opposed portion, said retaining segment being biased into contact with said outer segment of said at least one opposed portion with a passage being defined in said at least one opposed portion distally of said ramp segment for slidably receiving a structure through said at least one opposed portion, said retaining segment being movable away from said outer segment of said at least one opposed portion in response to movement of the structure from said passage along said ramp segment and between said retaining segment and said outer segment of said at least one opposed portion such that the structure is grasped between said retaining segment and said outer segment of said at least one opposed portion to fixedly secure said clip thereto.

10. A multifunctional clip as recited in claim 9 wherein said ramp segment is flexible to accommodate movement of said retaining segment away from said outer segment of said at least one opposed portion.

11. A multifunctional clip as recited in claim 10 and further including opposed slots in said outer segment of said at least one opposed portion aligned with said passage and through which the structure in said passage can pass to extend through said at least one opposed portion, said slots extending from said passage to said retaining segment to define tracks for movement of the structure from said passage to between said retaining segment and said outer segment of said at least one opposed portion.

12. A multifunctional clip as recited in claim 9 wherein said outer segment of said at least one opposed portion has an inwardly facing surface facing said retaining segment, said inwardly facing surface of said outer segment of said at least one opposed portion has a length between said proximal end of said at least one opposed portion and said distal end of said outer segment of said at least one opposed portion and said retaining segment is biased into contact with said inwardly facing surface of said outer segment of said at least one opposed portion along a substantial portion of said length.

13. A multifunctional clip as recited in claim 9 wherein said ramp segment terminates at a distal end disposed in contact with said outwardly facing surface of said inner segment of said at least one opposed portion.

14. A multifunctional clip as recited in claim 9 wherein said clip is biased to a grasping position wherein said first and second grasping surfaces are urged toward one another, is movable to a non-grasping position wherein said first and second grasping surfaces are moved away from one another to receive a structure therebetween and is movable from said non-grasping position toward said grasping position to grasp the structure between said first and second grasping surfaces.

15. In combination, a multifunctional clip and suture material for use in suturing in endoscopic and open operative procedures, said clip comprising a body having first and second opposed portions connected to one another at proximal ends of said first and second opposed portions, said first opposed portion including a first outer segment, a first inner segment extending from a distal end of said first outer segment toward said proximal end of said first opposed portion, said second opposed portion including a second outer segment, a second inner segment extending from a distal end of said second outer segment toward said proximal end of said second opposed portion, said first and second inner segments each being disposed between said first and second outer segments with said first and second outer and inner segments in alignment with one another, said first inner segment having a first outwardly facing surface facing said first outer segment and a first inwardly facing surface facing said second inner segment, said second inner segment having a second outwardly facing surface facing said second outer segment and a second inwardly facing surface facing said first inwardly facing surface such that said first and second inwardly facing surfaces define first and second grasping surfaces, respectively, at least one of said opposed portions having a retaining member extending distally from a proximal end of said inner segment of said at least one opposed portion, said retaining member being disposed between said outer and inner segments of said at least one opposed portions in alignment with said outer and inner segments of said at least one opposed portion, said retaining member being biased into contact with said outer segment of said at least one opposed portion, said at least one opposed portion having a passage therethrough adjacent said retaining member, said passage extending transverse to said retaining member, said suture material comprising a length of filamentous suture material slidably disposed in said passage such that said clip is movable longitudinally along said length of suture material, said retaining member being movable away from said outer segment of said at least one opposed portion to receive a segment of said length of suture material from said passage between said retaining member and said outer segment of said at least one opposed portion, said retaining member being movable toward said outer segment of said at least one opposed portion to grasp said segment of said length of suture material between said retaining member and said outer segment of said at least one opposed portion to fixedly secure said clip on said length of suture material, said clip being movable from a closed position to an open position to receive another segment of said length of suture material between said first and second grasping surfaces and from said open position toward said closed position to grasp said another segment of said length of suture material between said first and second grasping surfaces.

16. The combination recited in claim 15 wherein said clip is biased to said closed position and said retaining member is movable away from said outer segment of said at least one opposed portion to receive said segment of said length of suture material therebetween without moving said clip from said closed position to said open position.

17. The combination recited in claim 16 wherein said retaining member is flexible.

18. The combination recited in claim 17 wherein said retaining member includes a retaining segment biased into contact with said outer segment of said at least one opposed portion and an angled ramp segment extending inwardly from said retaining segment in the direction of said inner segment of said at least one opposed portion for facilitating movement of said segment of said length of suture material from said passage to between said retaining segment and said outer segment of said at least one opposed portion.

19. The combination recited in claim 18 and further including openings in said outer segment of said at least one opposed portion disposed at opposite ends of said passage, respectively, through which said length of suture material passes, said openings defining tracks, respectively, for movement of said segment of said length of suture material from said passage to between said retaining segment and said outer segment of said at least one opposed portion.

20. The combination recited in claim 19 and further including gripping formations on said retaining segment and said outer segment of said at least one opposed portion for gripping said segment of said length of suture material between said retaining segment and said outer segment of said at least one opposed portion.

* * * * *